United States Patent
Hall

(10) Patent No.: US 7,720,525 B2
(45) Date of Patent: May 18, 2010

(54) METHOD AND APPARATUS FOR COMBINING CONTINUOUS WAVE AND TIME DOMAIN OPTICAL IMAGING

(75) Inventor: David Jonathan Hall, Montreal (CA)

(73) Assignee: New Art Advanced Research Technologies Inc., St-Laurent (CA)

( * ) Notice: Subject to any disclaimer, the term of this patent is extended or adjusted under 35 U.S.C. 154(b) by 1962 days.

(21) Appl. No.: 10/386,132

(22) Filed: Mar. 12, 2003

(65) Prior Publication Data

US 2004/0181153 A1   Sep. 16, 2004

(51) Int. Cl.
*A61B 6/00* (2006.01)
(52) U.S. Cl. .................................. 600/473; 600/476
(58) Field of Classification Search ............... 600/473, 600/476
See application file for complete search history.

(56) References Cited

U.S. PATENT DOCUMENTS

| | | | | |
|---|---|---|---|---|
| 4,972,331 A * | 11/1990 | Chance | .................. | 600/310 |
| 5,371,368 A * | 12/1994 | Alfano et al. | .............. | 250/341.1 |
| 5,477,051 A * | 12/1995 | Tsuchiya | ................. | 250/341.1 |
| 5,772,588 A * | 6/1998 | Miwa et al. | ................ | 600/310 |
| 5,778,016 A * | 7/1998 | Sucha et al. | ............... | 372/38.1 |
| 5,782,755 A * | 7/1998 | Chance et al. | ............. | 600/322 |
| 5,853,370 A * | 12/1998 | Chance et al. | ............. | 600/473 |
| 6,321,111 B1 * | 11/2001 | Perelman et al. | ........... | 600/477 |
| 6,335,792 B1 * | 1/2002 | Tsuchiya | ................... | 356/432 |
| 6,339,216 B1 * | 1/2002 | Wake | ..................... | 250/214 A |
| 6,992,762 B2 * | 1/2006 | Long et al. | ................ | 356/317 |
| 7,047,057 B2 * | 5/2006 | Hall et al. | .................. | 600/407 |
| 2003/0023172 A1 * | 1/2003 | Tromberg et al. | ........... | 600/476 |
| 2003/0030809 A1 * | 2/2003 | Boas et al. | ................. | 356/432 |
| 2005/0187478 A1 * | 8/2005 | Beaudry et al. | ............ | 600/476 |

FOREIGN PATENT DOCUMENTS

| | | |
|---|---|---|
| EP | 0385608 A1 * | 5/1990 |
| EP | 0 385 608 A1 | 9/1990 |
| EP | 0 656 537 A1 | 6/1995 |
| EP | 0656537 A1 * | 7/1995 |
| EP | 0656537 A1 * | 7/1995 |
| WO | WO 02/41760 A2 | 5/2002 |
| WO | WO 0241760 A2 * | 5/2002 |
| WO | WO 03/008945 A1 | 1/2003 |

OTHER PUBLICATIONS

Chance, B. "Time Resolved Spectroscopic (TRS) and Continuous Wave Spectroscopic (CWS) Studies of Photon Migration in Human Arms and Limbs", Advances in Experimental Medicine and Biology, vol. 248, 1989, pp. 21-31, XP009031780.

* cited by examiner

*Primary Examiner*—Brian Casler
*Assistant Examiner*—Peter Luong
(74) *Attorney, Agent, or Firm*—Day Pitney LLP

(57) ABSTRACT

There is provided methods and systems for optical imaging in a turbid medium that combine continuous wave (CW) and time domain (TD) approaches to substantially increase robustness of optical imaging as well as to reduce acquisition times associated with the TD approach. In one aspect, a method is provided that uses CW measurements to scale the values of a temporal point spread function (TPSF) to avoid physical unit mismatch problems. In another aspect, both CW and TD measurements are synergistically combined to estimate optical properties of the medium used in image reconstruction. Optical systems capable of realizing these methods are also provided.

30 Claims, 3 Drawing Sheets

METHOD AND APPARATUS FOR COMBINING CONTINUOUS WAVE AND TIME DOMAIN OPTICAL IMAGING

CROSS-REFERENCE TO RELATED APPLICATIONS

This is the first application filed for the present invention.

TECHNICAL FIELD

The invention relates to the field of optical imaging of turbid media, such as mammalian tissue. More specifically, the invention relates to optical imaging using both continuous wave and time domain methods.

BACKGROUND OF THE INVENTION

Imaging of mammalian tissues has been used extensively to obtain information on the internal structures as well as on the biodistribution of molecules. This information can of course be utilized for diagnosis purposes. Several techniques based on different physical principles are currently available to obtain images that encompass a broad range of spatio-temporal resolution. Such techniques include Magnetic Resonance Imaging (MRI), Positron Emission Tomography (PET), single-photon emission computed tomography (SPECT), X-ray, ultrasound and, now emerging, optical imaging.

In optical imaging three approaches have been used to generate the optical data necessary to reconstruct images of volume of interest (VOI) namely Continuous Wave (CW), which involves the measurement of light attenuation; Time Domain (TD), which involves injecting a pulse of light of short duration within the VOI and detecting the light as a function of time as it exits the VOI; and Frequency Domain (FD), which relies on frequency modulation of the light source and analysis of the phase and amplitude of the signal as it exits the VOI.

Continuous wave permits rapid acquisition and is the least expensive of the three approaches but provides a limited amount of information. More specifically, in CW imaging, the scatter coefficient of the VOI must be an assumption in order to obtain absorption coefficient information. CW cannot determine absorption separately from scatter. TD provides more information. In TD, a short laser pulse is injected in the part of the mammal to be imaged and the distribution of the time of flight of the photon exiting the volume of interest is measured. The resulting signal is referred to as a temporal point spread function (TPSF) that can be used to calculate such characteristics as the mean time of flight of photons. In FD, the intensity of the source is modulated with high frequency. As a result, a photon density wave propagates in the tissue and the amplitude and phase shift of the wave relative to the incident wave is measured. In principle, by scanning the tissue with a range of different frequencies, the entire TPSF can be reconstructed. However, in practice, a single frequency is usually employed to estimate the mean time of flight of the photons.

Image reconstruction using optical data belongs to the class of inverse problems. The problem consists of finding the distribution of optical parameters in tissue based on the detected optical signal. While image reconstruction techniques are still the subject of intense research activities, several tested approaches have been used with relative success. Some of these approaches are summarized and described in Boas et al. (IEEE SiG. Proc. Mag., Vol. 18, No. 6, pp. 57-75, 2001) and Hawrysz and Sevick-Muraca (Neoplasia, Vol. 2, No. 5, pp 388-417, 2000).

TD measurements provide detailed information about the absorption and the scatter from within a tissue, however, the method suffers from long acquisition time, expensive hardware and complicated software analysis. Furthermore the acquisition often results in noisy TPSF data from which accurate estimates of spatial optical information are difficult to obtain.

It would therefore be desirable to provide a method that would overcome the limitations of CW and TD, while retaining their advantages.

SUMMARY OF THE INVENTION

The inventor has provided a method and apparatus by which the advantages of TD optical imaging can be exploited while avoiding certain disadvantages. In particular long acquisition times can be substantially reduced.

In one aspect of the invention there is provided a method for optical imaging of a volume of interest (VOI) in a turbid medium, the method comprising:

optically scanning the VOI at a plurality of source/detector geometries using continuous wave (CW) to generate a measured attenuation value at one or more wavelength, the measured attenuation value being measured from a continuous light intensity value provided to the source and detected at the detector;

optically scanning the VOI using time-domain (TD) to generate data representing at least a portion of a measured temporal point spread function (TPSF) at the one or more wavelength, the TPSF data being measured for each of the plurality of source/detector geometries from a plurality of light pulses from which a statistical average of light received as a function of time is obtained, the TPSF data yielding information about absorption and scatter within the VOI; and combining information provided by CW and TD, whereby to generate an improved image of the VOI with fewer light pulses and a shorter acquisition time by using both time-domain and continuous wave modalities.

In another aspect of the invention there is also provided an optical imaging apparatus for imaging a turbid media object, the apparatus comprising: at least one optical source for providing continuous and pulsed optical energy; at least one optical detector for detecting optical energy and generating time-dependent and continuous data; a source/object optical coupling for coupling the optical source to a desired position on the object; a detector/object optical coupling for coupling the optical detector to a desired position on the object; an acquisition controller connected to the optical source and the optical detector for collecting the time-dependent and continuous data for a plurality of source/detector geometries within a volume of interest in the object; a raw TPSF data compiler for receiving a time-dependent output signal from the detector and generating raw TPSF data output; a TPSF data enhancer for processing the raw TPSF data output and the continuous data to provide enhanced TPSF data, wherein the continuous data corresponds to the raw TPSF data output according to the source/detector geometries.

It will be appreciated that the present invention allows for a number of different possible economies to be achieved by combining CW with TD techniques. Firstly, the estimate of absorption coefficients for a VOI from CW (making an assumption about scatter, such as assuming that scatter is constant for example) can be used as initial values in processing the TD data to yield more accurate absorption coefficients (along with scatter coefficients). Secondly, the process of determining the optical properties of the VOI can involve simultaneously comparing CW model data with CW measured data and comparing TD model data with TD measured data. Thirdly, processing time and acquisition time can be reduced by using an image generated from CW data alone as a less-accurate image, whose purpose is to help in defining a subset of source/detector configurations or geometries to be used in collecting TD data for specific portions of the VOI requiring better detail.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

In the present description, by CW measurements it is meant optical signals measured while the light source that illuminates the object to be imaged is continuously on, namely a steady state flux measurement.

By Time Domain (TD) measurements, it is meant that the optical signal is measured as a function of time following a brief pulse of the light source. The resulting signal is the so-called temporal point spread function (TPSF), and the TPSF data collected may be either one, two, a few or several points on the TPSF (often referred to as different time gates), a single parameter resulting from a plurality of points, such as a slope or other characteristic of the TPSF curve, or the whole TPSF data. When the TD optical detector is a single-photon counting detector, the whole TPSF can be efficiently collected as a result of the measurement technique. When a gated ICCD is used, it is more practical to select time gates. Due to the nature of the detection system, the TPSF data requires a large number of acquisitions (and in comparison to CW, much more time) to achieve relatively stable measured values. In many cases, the TPSF data will be inherently noisy.

Optical image reconstruction can be based on complex photon propagation models such as Boltzmann transport equation (Arridge, Inv. Prob., Vol. 15, pp. R41-R93, 1999) or on simpler model photon diffusion (migration) equations which incorporate an optical diffusion coefficient, D, which is a function of absorption coefficient $\mu_a$ and the modified scatter coefficient $\mu_s'$. Based on these equation and optical signal measurements, $\mu_a$ and $\mu_s'$ can be estimated and therefore provide a spatial distribution of these optical properties within the object (Hawrysz and Sevick-Muraca, Neoplasia, Vol. 2, No. 5, pp 388-417, 2000).

Photon diffusion equation can be solved using both CW and TD measurements to predict the photon fluence based on known spatial distribution of $\mu_a$ and $\mu_s'$ with the difference that there is no time dependence for the CW case. However, if these properties are not known a priori they must be calculated or estimated. TD measurements with appropriate processing of the data can yield $\mu$'s information, but as mentioned previously requires longer acquisition times. CW measurements are faster and more economical but cannot distinguish between $\mu_a$ and $\mu_s'$.

Figure 1:
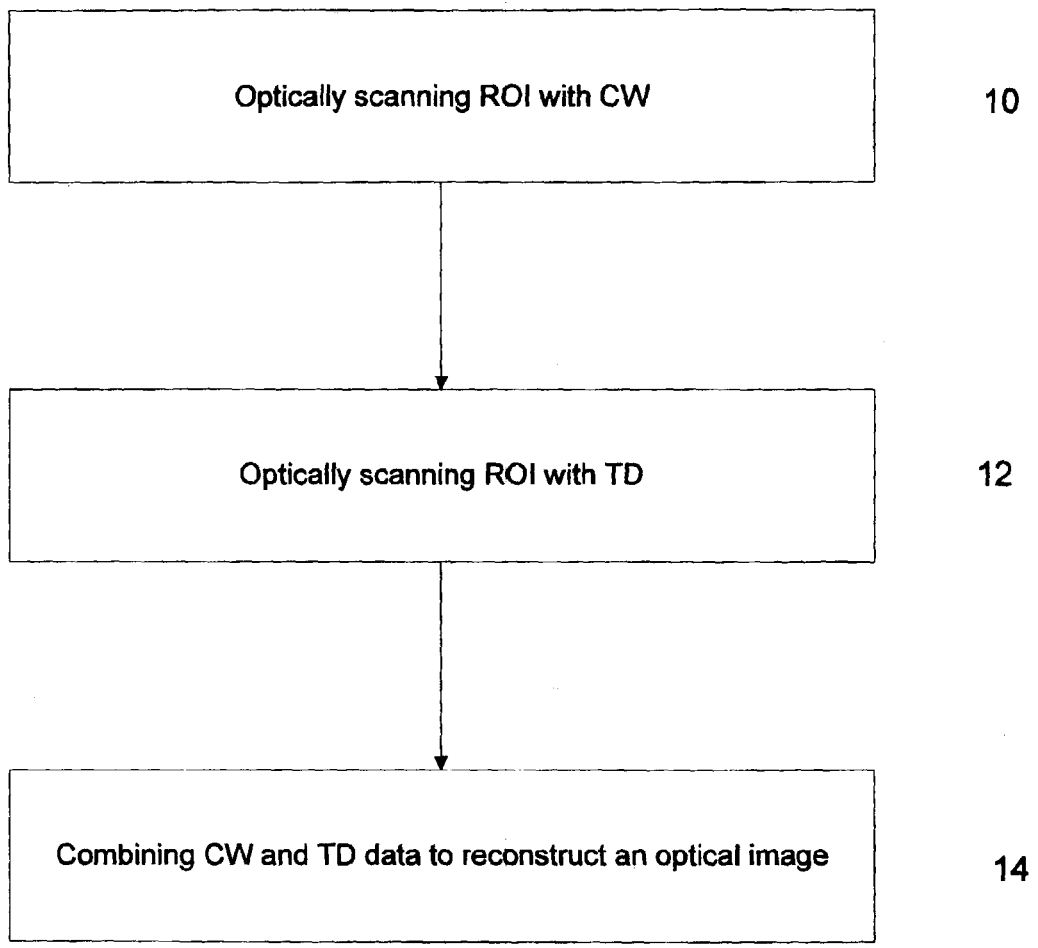
FIG. 1 is a high-level flow chart illustrating the general method according to some embodiments of the present invention.

In one aspect of the invention, there is provided a method that advantageously combines CW and TD measurements without some of their disadvantages to produce optical images. Thus and referring to FIG. 1, CW and TD data are acquired at 10 and 12 over a given part of an object such as a mammal comprising a volume of interest (VOI) to obtain an attenuation value and a TPSF, and are combined at 14 to produce an image of the VOI. The combination of the data from the two measurement modes permits a more accurate image reconstruction and can also result in substantially reduced acquisition times.

In one embodiment of the invention the optical properties $\mu_a$ and $\mu_s'$ are estimated using both CW and TD measurements obtained independently, namely without necessarily having the same source/detector geometries. The resulting values of $\mu_a$ and $\mu_s'$ obtained with each modality are compared and are reciprocally adjusted until the difference is less than a predetermined value. In other words, the values of $\mu_a$ and $\mu_s'$ are iteratively adjusted for one modality by taking into account the values obtained with the other modality. This approach advantageously reduces the acquisition times for TD measurements by providing additional information with CW allowing acquisition of TPSF with lower S/N ratios. Alternatively CW and TD data can also be combined to estimate $\mu_a$ and $\mu_s'$ as opposed estimating $\mu_a$ and $\mu_s'$ with each modality.

It will be appreciated that iteration may be saved if the estimate of $\mu_a$ by way of CW imaging is used as a starting point for determining $\mu_a$ and $\mu_s'$ by way of TD imaging. Furthermore, the process of imaging and calculating the values for $\mu_a$ (i.e. by making an assumption about $\mu_s'$, for example by holding $\mu_s'$ constant) by CW can be carried out in parallel with the acquisition of TPSF data. Preferably, the CW imaging will be completed before the TD data acquisition is completed and determination of $\mu_a$, $\mu_s'$ values begin using the TPSF data. In this way, the $\mu_a$ data determined by CW can be used as an initial best guess in the TD imaging. Of course, the collection of CW data for the various source/detector geometries as is needed by the CW data processing unit may require little time in comparison with the CW data processing time. Provided that TD data acquisition can continue in parallel with the processing of the CW data, parallel imaging can be provided.

Figure 2:
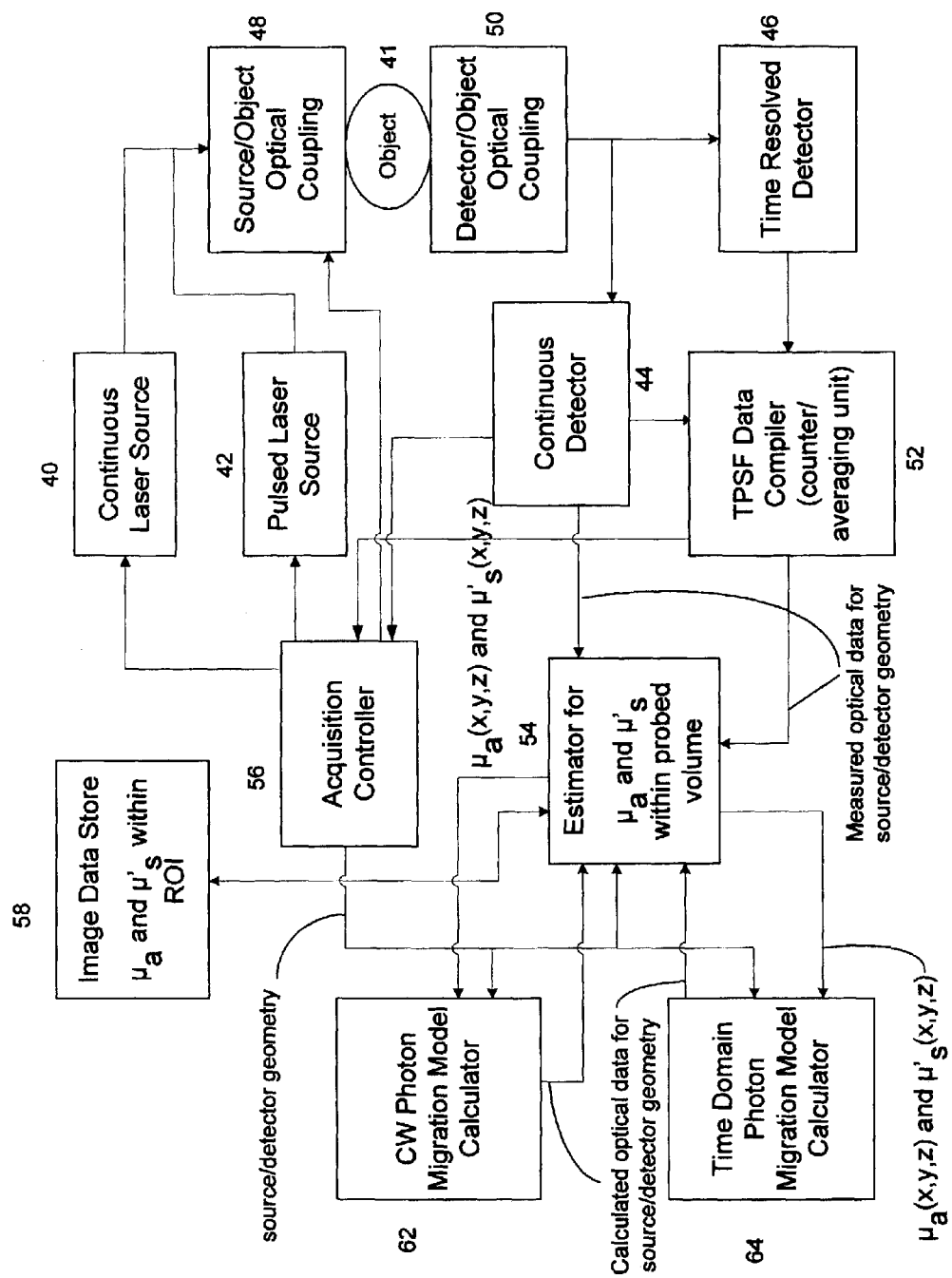
FIG. 2 is a block diagram of an imaging apparatus according to another embodiment of the invention in which CW data is used to help in determining optical properties of a VOI of an object being imaged using TPSF data and a TD photon migration model.

The above embodiments of the method of the invention can be carried out using a system as described in FIG. 2 in which a combination of CW and TD modalities is described that synergistically integrates the two approaches to provide faster and more accurate estimates of the optical properties of an object. In this regard, a continuous 40 and a pulsed 42 laser source are provided to inject light within an object 41. Also provided are one or more detectors suitable for CW 44 and TD 46 detection. The optical coupling of the sources and detectors at 48 and 50 respectively with the object to provide desired source/detector configurations can be realized using known technologies such as optical fibers, free-space optics and the like.

The controller 56 has a control output signal to coupling device 48 for selecting the source position. This is preferably achieved by way of an optical switch in the case of a fiber optic coupling, and in the case of free-space optics by way of a galvo-mirror inserted within the optical system. The detector coupling device 50 preferably requires no switching control. This is achieved in the case that the detector has a channel for each detector position, as is practical in the case of a gated ICCD. However, when using free-space optics, the detector position is controlled by galvo-mirror or other means to achieve movement of the detection spot over the object.

The time resolved detector 46 is linked to a raw TPSF data compiler 52 that can generate TPSF's. Compiler 52 may also comprise a normalizer unit wherein TPSF data can be normalized by the CW data (attenuation) to produce dimensionless data to avoid, for example, experiment-to-theory unit mismatch thereby enabling quick processing of the data. An estimator 54 is provided to estimate values for $\mu_a$ and $\mu_s'$ from the measured optical data and the calculated optical data for the given source/detector geometry. The calculated CW optical data is provided by a calculator 62, while the calculated TD optical data is provided by a calculator 64. In the embodiment of FIG. 2, the TPSF data acquired and enhanced may be the full TPSF, a TPSF characteristic parameter, or a plurality of time-gate TPSF points.

The modes (CW or TD) and the sequences of data acquisition are controlled by an acquisition controller 56. In particular the acquisition controller can advantageously dynamically control the acquisition of data based on the information received by the detectors. Once the acquisition is completed the image data is stored in raw image data store 58.

It will be appreciated that the system can be modified and still achieve similar results. For example, a single laser source that can provide a continuous as well as pulsed output can be used. Also a single detector can be used to detect continuous or time resolved signals. Other modifications as would be obvious to one skilled in the art are also considered to be within the scope of the invention.

The apparatus of FIG. 2 can be used in a variety of ways. Firstly, the estimator 54 can process CW data for a VOI. This is done by making an assumption about $\mu_s'$ value for the whole VOI. While this assumption may be wrong, it allows for an estimation of $\mu_a$ that is close in some cases, and at least a useful first approximation in other cases. The resulting 3D map of $\mu_a$ and $\mu_s'$ stored in store 58 would have the assumed $\mu_s'$ values (which could be constant values), and a first approximation of $\mu_a$. In estimating both $\mu_a$ and $\mu_s'$ using the TD optical data, the assumed $\mu_s'$ value and the first approximation of the $\mu_a$ values is are fed to calculator 64. The estimator 54 will compare the resulting calculated TPSF optical data to the measured TPSF data to determine in a first pass an adjustment to both $\mu_a$ and $\mu_s'$. This may be done for more than one TPSF time gate in the case that time gate values are used. The mode of operation allows for the possibility of acquiring cW data and processing it to obtain the first approximation of $\mu_a$ for the whole VOI or object, while acquisition of raw data on the TD side continues during CW calculation time (but not during CW data acquisition unless parallel optical data acquisition hardware is provided).

Secondly, the estimator 54 can compare the CW and TD calculated and measured optical data together and decide on a best value for $\mu_a$ and $\mu_s'$. In this case, the calculator 62 uses the $\mu_a$ and $\mu_s'$ data in which there is no assumption about $\mu_s'$ values. Since the CW data is less noisy, a better estimate of $\mu_a$ and $\mu_s'$ is obtained using both the CW and TD data than with the TD data alone. While this second approach may be done wholly simultaneously, namely CW and TD acquisition and data processing together, it may also be done following a first CW pass as in the first approach.

Thirdly, it will be appreciated that the apparatus of FIG. 2 can be used to obtain a CW image prior to imaging by TD. In this case, the CW image may be used to select a specific portion of the object 41 that would require better resolution by TD imaging. In this case, an input to the acquisition controller 56 (not shown) is provided to select the specific VOI to be imaged by TD. The CW-based image data in store 58 would then be enhanced by the TD data. Again, for the specific VOI, the CW data could be re-measured or retrieved from a data store (not shown) and used in conjunction with the TD data to enhance image reconstruction. By reducing the volume to image by TD, image acquisition and reconstruction data processing time is saved.

For example CW can be used to find a lesion (VOI) within a breast, while TD measurements can be used to reveal finer details about the spatial distribution of optical properties within the lesion that may be helpful in diagnosing the breast lesion. This strategy of data acquisition may also be used for example to find the biodistribution of a compound by CW, while TD measurements of the regions comprising the compound may serve to calculate the concentration of the compound.

The TD and CW data can be acquired either sequentially or simultaneously. Sequential acquisition may be achieved for example by using a time-gated intensified CCD camera. This type of camera provides the capability for measuring optical signals both in the CW and TD modes. The CW mode data can be acquired by simply turning the time gate off. Alternatively TD and CW data can be acquired using optic components that are exclusively designed for one mode.

Advantageously, the CW and TD data can be acquired using a gated ICCD camera. The advent of the gated intensified charged coupled device (ICCD) has permitted that significant number of time-domain spatial measurements be performed simultaneously. Moreover, when the gate is turned off the camera works in a CW mode, thus obviating the need for a separate CW and TD hardware. An image sequence of CW mode, TD mode data acquisition can thus be obtained Simultaneous acquisition may be achieved by acquiring the TD and CW data at different wavelengths thereby permitting spectral discrimination and simultaneous acquisition. In this case the acquisition of the optical signal is performed at a plurality of wavelengths and the CW and TD data are combined to reconstruct an image.

In a preferred embodiment certain specific time points or intervals of time (time gates) of the TPSF at which TD data will be acquired are selected. The determination of the time gates is preferably based on the following approach:

A noiseless TPSF is a continuous and infinitely differentiable function defined on $R^+$. Critical points of a function can be identified via zeros of this function's derivative. Due to the fact that a TPSF has a characteristic shape, the $i^{th}$ derivative will yield a set of points where the derivative became zero, which corresponds to extreme values of the underlying function. The first subset $s_1=\{s_{1,1}\}$ corresponding to the $1^{st}$ derivative describes the unique TPSF maximum. The second subset $s_2=\{s_{2,1}; s_{2,2}\}$ corresponding to the $2^{nd}$ derivative reveals two points where the curvature directionality changed. Derivatives of the higher order yield information on more subtle details of the TPSF shape. The subset $s_i$ can be defined as $s_i=\{s_{i,1}; \ldots; s_{i,i}\}$ for the case of continuous TPSF.

Given a TPSF f(x) represented with a set of M values (M>>N), confined within an interval $[a_o, b_o]$ one can perform recursive numerical "differentiation" of the TPSF and of its' "derivatives" by computing the quotient:

$$Q_i = \frac{f(x_{i+1}) - f(x_{i-1})}{x_{i+1} - x_{i-1}}, \ x_i \geq a_0, x_M \leq b_0$$

which would approximate the value of $f'(x_i)$.

Figure 3A:
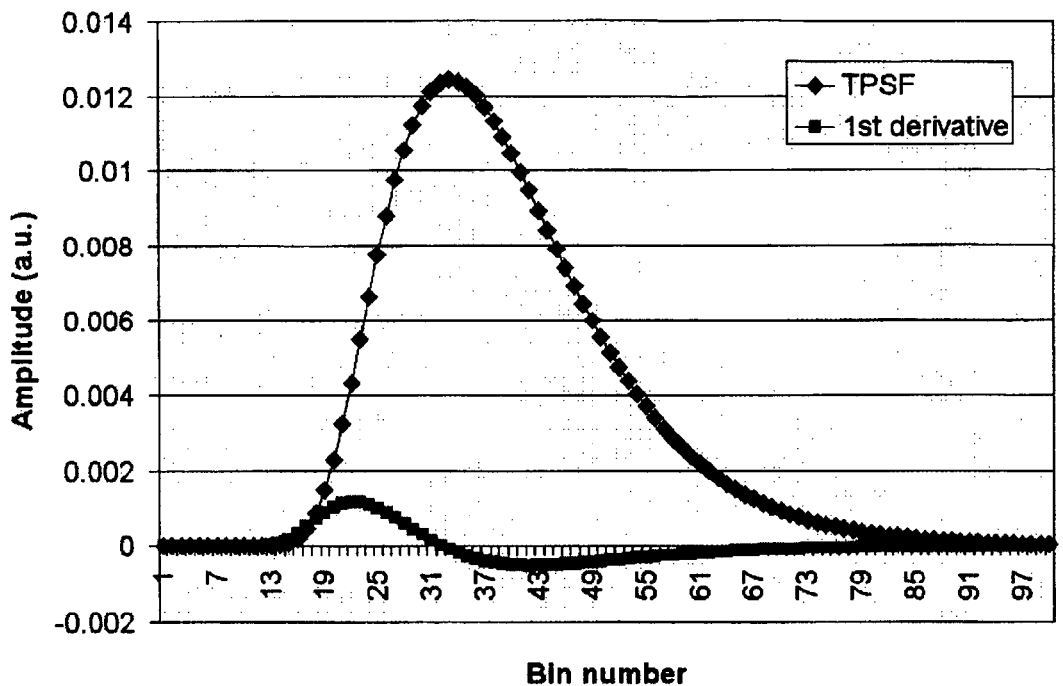
FIG. 3a is a plot of amplitude vs time (bin number) for a TPSF and its first derivative.
Figure 3B:
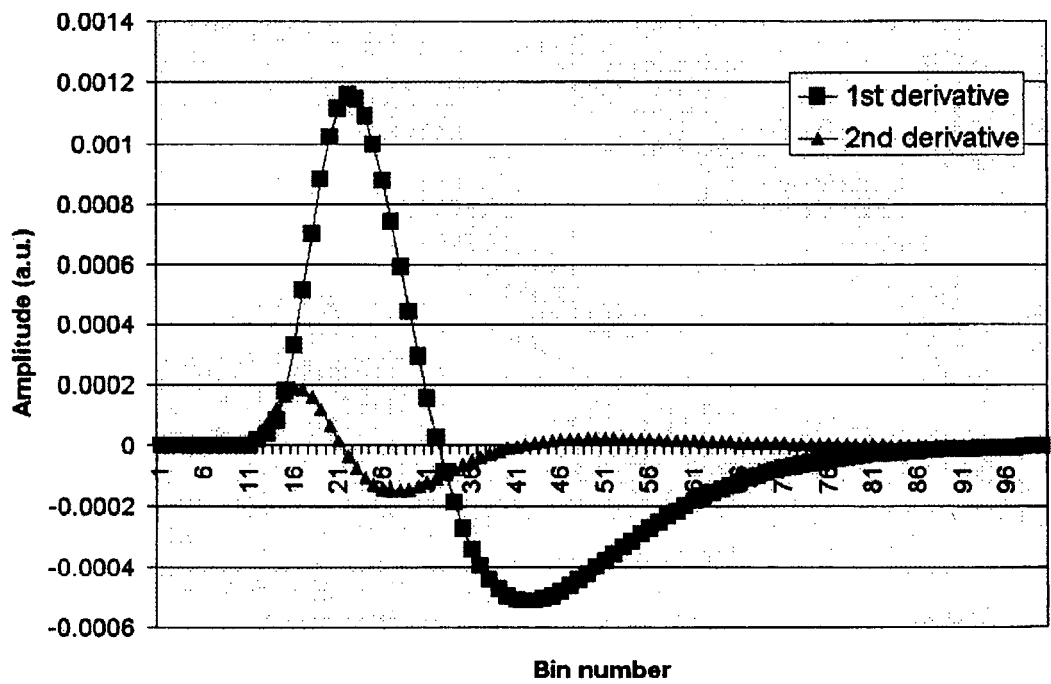
FIG. 3b is a plot of amplitude vs time (bin number) for the first derivative of a TPSF and its second derivative.

When plotted, characteristic sequence of functions will emerge as shown in FIGS. 3A and 3B. In this example, one observes that: $s_1=\{31.5\}$, $s_2=\{20.5; 40.5\}$, $s_3=\{14.5; 25.5; 48.5\}$.

In order to obtain an adequate TPSF representation with N points or time gates, one would want to reflect the TPSF shape as fully as possible. The sequence of numbers $\{s_1; s_2; \ldots\}$ allows for identification of the most relevant points in the order of diminishing significance as the subset number increases. Elements within a given subset $s_i$ have equal significance.

One can replace $s_i$ with:

$$s_i' = \{(s_{i,1}-0.5r, s_{i,1}+0.5r); \ldots; (s_{1,i}-0.5r, s_{i,i}+0.5r)\}$$

where r is the width of a time gate. The set $s_i'$ is a collection of intervals rather than points.

In the case where several partial TPSF's are to be acquired, when for example different source-detector configurations are used, the procedure outlined above can yield $S^i=\{s_1^i; s_2^i; \ldots\}$; $i=1,\ldots,K$ for a given TPSF where K is chosen a priori. In order to reflect the most relevant features of the set of TPSFs, the union of the nth derivative zeros is obtained. For example $S_1 = s_1^1 \cup s_1^2 \cup \ldots \cup s_1^k$, $S_2 = s_2^1 \cup s_2^2 \cup \ldots \cup s_2^k$ and so on. The set $\{S_1; S_2; \ldots\}$ provides a sequence of numbers that should be used to represent the set of K TPSFs in an optimal manner.

As above, $s_i$ might be replaced with $s_i'$ in order to analyze time gates instead of time points.

In one embodiment of the invention the steps to select the appropriate time points or time gates are as follows:

Acquire TPSFs with high temporal resolution for all source-detector pairs that are capable of functioning simultaneously. At least one typical source position should be used. Robustness of the subsequent analysis increases, as more typical source positions are included.

Approximate all measured TPSFs with curves based on a model of photon propagation.

Perform analysis as described above to determine the N time gates to be used during acquisition.

Acquire data with the N points of the set $\{S_1; S_2; \ldots\}$.

Preferably N is an input parameter. In practice it will be determined via estimation of the resulting data set size that can be used to reconstruct images within desired time frame. One might want to estimate N as well in case data set size is not an issue.

Time window $[a_0,b_0] \subset R^+$ used for initial data acquisition is assumed an input parameter. However, it should be chosen wide enough based on prior knowledge in order to maximize chances of capturing most significant TPSF features.

Temporal sampling, i.e. the distance between $x_i$ and $x_{i+1}$ is an input parameter.

Temporal resolution $r_0$, i.e. the minimal distance between $x_i$ and $x_{i+1}$ that yields "uncorrelated" values $f(x_1)$ and $f(x_{i+1})$, comes primarily from the limitations of the data acquisition hardware and is, therefore, an input parameter.

It is preferable to perform initial data acquisition with the steps of not more than $0.5 \times r_0$ and time gate width of not more than $r_0$. Eventual time gate width $r \geq r_0$ might be chosen to minimize data set size while preserving the distinct TPSF features revealed by the analysis. For example, distinct points $s_{i,j}$ and $s_{i',j'}$ would fall within the same time gate if $|s_{i,j}-s_{i',j'}|<r$.

The use of variable time gate widths may yield superior results. One would replace $s_i'$ with $s_i'' \equiv \{(s_{i,1}-0.5r_{i,1}, s_{i,1}+0.5r_{i,1}); \ldots; (s_{i,i}-0.5r_{i,i}, s_{i,i}+0.5r_{i,i})\}$ to analyze this case.

The selected time gates may be used to reconstruct the TPSF. Constraints may be used in the reconstruction. For example, the integrated TPSF may be constrained to a value substantially identical to a measured attenuation value obtained by CW measurements. Further, the number of time points or time gates that is necessary to acquire in order to reconstruct an acceptable image is reduced because of the additional information conveyed by the CW measurements.

With partial TPSF acquisition, gated ICCD camera may allow acquisition of CW and TD data according to predetermined sequences as would be obvious to one skilled in the art. Zoom lenses may also be used to obtain CW data in full field mode and TD data by zooming in on a desired VOI.

The embodiment(s) of the invention described above is(are) intended to be exemplary only. The scope of the invention is therefore intended to be limited solely by the scope of the appended claims.

I claim:

1. A method for optical imaging of a volume of interest (VOI) in a turbid medium, the method comprising:
   i) optically scanning the VOI at a plurality of source and detector geometries using continuous wave (CW) to generate CW data;
   ii) optically scanning the VOI at a plurality of source and detector geometries using time-domain (TD) to generate data representing at least a portion of a measured temporal point spread function (TPSF), said TPSF data being measured from a plurality of light pulses from which a statistical average of light received as a function of time is obtained, said TPSF data yielding information about absorption and scatter within said VOI;
   iii) combining information extracted from the CW data with the TPSF data to improve an accuracy of imaging using the measured TPSF data whereby an improved image accuracy of the VOI of the turbid medium is generated with fewer said light pulses and a shorter acquisition time by using both time-domain and continuous wave modalities; and
   iv) generating an improved image of the VOI of the turbid medium.

2. The method as claimed in claim 1 further comprising a step of normalizing said measured TPSF data relative to said CW data prior to combining the information to generate dimensionless data thereby providing quicker data processing.

3. The method as claimed in claim 1 further includes measuring sequentially the TPSF and CW data.

4. The method as claimed in claim 1 further includes using a gated ICCD camera to measure the TPSF and CW data, and providing from each said light pulse an intensity value within at least one selected time gate.

5. The method as claimed in claim 1 further includes measuring at a plurality of wavelengths the TPSF and CW data and acquiring simultaneously at different wavelengths the TPSF and attenuation value.

6. The method as claimed in claim 1 further includes measuring a partial TPSF.

7. The method as claimed in claim 6 wherein the step of measuring the partial TPSF further includes measuring the partial TPSF that comprises one or more predetermined time gate.

8. The method as claimed in claim 1 wherein the step of combining comprises:
   a) estimating a value of one or more optical property within the VOI using the measured TPSF;
   b) calculating an attenuation value using the estimated optical properties;
   c) comparing the calculated attenuation value with the CW data to obtain a difference value; d) repeating steps a) through c) until the difference value is less than a predetermined value.

9. The method as claimed in claim 8 wherein said step of calculating comprises using a CW photon migration model.

10. The method as claimed in claim 1 wherein said step of combining comprises:
   estimating a value of one or more optical property using TD measurements; estimating said value of one or more optical property using CW measurements;
   comparing said value of one or more optical property obtained by TD with said one or more optical property obtained by CW; and
   adjusting said CW and TD estimations of said value of one or more optical property until said estimations converge to a predetermined range.

11. The method as claimed in claim 10 wherein the estimating value step further includes said one or more optical property is selected from absorption coefficient, scattering coefficient and a combination thereof.

12. The method as claimed in claim 11 wherein said one or more optical properties in the estimating value step are said absorption coefficient and said scatter coefficient and wherein prior to estimating a value of said absorption and scatter coefficients using TD measurements, said absorption coefficient is estimated using CW measurements while keeping said scatter coefficient constant.

13. A method for optical imaging of a volume of interest (VOI) in a turbid medium, the method comprising:
   i) obtaining continuous wave (CW) data to generate an image of a part of the medium comprising the VOI;
   ii) generating the image of the part of the medium comprising the VOI;
   iii) localizing the VOI within the part of the medium using information from the generated image;
   iv) obtaining time-domain (TD) data from the localized VOI to generate an image of the localized VOI in the turbid medium; and
   v) generating the image of the localized VOI in the turbid medium.

14. A method for optical imaging of a volume of interest (VOI) in a turbid medium, the method comprising:
   i) obtaining continuous wave (CW) data to generate an image of a part of the medium comprising the VOI;
   ii) generating the image of the part of the medium comprising the VOI;
   iii) localizing the VOI within the part of the medium using information from the generated image;
   iv) optimizing TD image acquisition parameters using the CW data;
   v) obtaining TD data from the VOI using the optimized TD image acquisition parameters to generate an image of the localized VOI in the turbid medium; and
   vi) generating the image of the localized VOI in the turbid medium.

15. The method as claimed in claim 14 wherein said step of optimizing comprises selecting one or more source and detector geometries used to generate CW data for use in obtaining TD data of the VOI.

16. An optical imaging system for imaging a turbid media object, the apparatus comprising:
   at least one optical source for providing continuous and pulsed optical energy;
   at least one optical detector for detecting optical energy and generating time-dependent and continuous data;
   a first optical coupling for coupling said optical source to a desired position on said object;
   a second optical coupling for coupling said optical detector to a desired position on said object;
   an acquisition controller connected to said optical source and said optical detector for collecting said time-dependent and continuous data for a plurality of geometries within a volume of interest in said object;
   a continuous-wave photon migration model calculator;
   a time-domain photon migration model calculator; and
   an estimator using said continuous data and calculated values corresponding to said continuous data to improve a determination of optical properties of said object using said time-dependent data and calculated values corresponding to said time-dependent data.

17. The system as claimed in claim 16 wherein said source comprises one or more laser source.

18. The system as claimed in claim 16 wherein said first optical couplings comprise a plurality of light injection ports and collection ports for coupling said optical source and said optical detector respectively with said tissue.

19. The system as claimed in claims 16 wherein said acquisition controller is coupled to an image data store, and used to adjust said optical source intensity as a function of said detected optical energy for optimizing signal to noise ratio.

20. The system as claimed in claim 16 further comprising a display for displaying a reconstituted image of said tissue.

21. The system as claimed in claim 16 further comprising means for selecting one or more detection wavelength.

22. The system as claimed in claim 21 wherein said means for selecting is a filter.

23. The system as claimed in claim 16 further comprising a raw TPSF data compiler for receiving a time-dependent output signal from said detector and generating raw TPSF data output.

24. The system as claimed in claim 23 wherein said TPSF data compiler comprises a TPSF data normalizer for normalizing said TPSF data with said continuous data.

25. The system as claimed in claim 16 wherein said optical source is a laser source to provide optical energy at a plurality of wavelengths simultaneously.

26. The system as claimed in claim 25 wherein said optical detector is a continuous detector and a time resolved detector for detecting optical energy at a plurality of wavelengths simultaneously.

27. The system as claimed in claim 16 wherein said first and second optical couplings for coupling said optical source and said optical detector with said object are selected from fiber optics, free-space optics and a combination thereof.

28. The system as claimed in claim 27 wherein said first and second optical couplings comprise a plurality of fiber optics and optical switches to select desired fiber optics for light injection and detection.

29. The system as claimed in claim 27 wherein said first and second optical couplings are free-space optics and wherein said free-space optics comprise mirrors to directionally propagate light so that the light is injected and collected from desired areas on said object.

30. The system as claimed in claim 29 wherein said mirrors are mirrors galvanometers.

* * * * *